(12) United States Patent
Savola et al.

(10) Patent No.: US 8,653,122 B2
(45) Date of Patent: Feb. 18, 2014

(54) OROMUCOSAL FORMULATION AND PROCESS FOR PREPARING THE SAME

(75) Inventors: Juha-Matti Savola, Turku (FI); Päivi Juujärvi, Littoinen (FI); Jukka Ilkka, Kuopio (FI)

(73) Assignee: Santhera Pharmaceuticals (Switzerland) Ltd., Liestal (CH)

( * ) Notice: Subject to any disclaimer, the term of this patent is extended or adjusted under 35 U.S.C. 154(b) by 1159 days.

(21) Appl. No.: 10/534,091

(22) PCT Filed: Nov. 10, 2003

(86) PCT No.: PCT/FI03/00850
§ 371 (c)(1),
(2), (4) Date: May 6, 2005

(87) PCT Pub. No.: WO2004/041271
PCT Pub. Date: May 21, 2004

(65) Prior Publication Data
US 2006/0052429 A1    Mar. 9, 2006

(30) Foreign Application Priority Data
Nov. 8, 2002 (FI) .................................. 20022007

(51) Int. Cl.
*A61K 31/415* (2006.01)
*A61K 9/14* (2006.01)

(52) U.S. Cl.
USPC ............................................ 514/396; 424/45

(58) Field of Classification Search
USPC ............................................ 514/396; 424/45
See application file for complete search history.

(56) References Cited

U.S. PATENT DOCUMENTS

| | | | |
|---|---|---|---|
| 4,855,326 A | 8/1989 | Fuisz | 514/777 |
| 5,079,018 A | 1/1992 | Ecanow | 426/385 |
| 5,298,261 A | 3/1994 | Pebley et al. | 424/488 |
| 5,434,177 A | 7/1995 | Riekkinen et al. | 514/399 |
| 5,466,464 A | 11/1995 | Masaki et al. | 424/434 |
| 5,498,623 A | 3/1996 | Karjalainen et al. | 514/396 |
| 5,541,211 A | 7/1996 | Pertovaara et al. | 514/396 |
| 5,658,938 A * | 8/1997 | Geerts et al. | 514/400 |
| 5,948,430 A | 9/1999 | Zerbe et al. | 424/435 |
| 6,284,270 B1 | 9/2001 | Lagoviyer et al. | 424/464 |
| 6,316,026 B1 | 11/2001 | Tatara et al. | 424/464 |
| 6,326,401 B1 * | 12/2001 | Chauveau et al. | 514/547 |
| 6,375,982 B1 | 4/2002 | Cherukuri | 424/484 |
| 6,413,988 B1 * | 7/2002 | De Proost | 514/320 |
| 6,552,024 B1 | 4/2003 | Chen et al. | 514/252.16 |
| 6,669,957 B1 | 12/2003 | Laruelle et al. | 424/465 |
| 6,696,085 B2 | 2/2004 | Rault et al. | 424/464 |
| 2004/0236108 A1 * | 11/2004 | Smith et al. | 544/406 |

FOREIGN PATENT DOCUMENTS

| | | |
|---|---|---|
| EP | 0 204 045 | 12/1986 |
| EP | 0 914 818 | 5/1999 |
| GB | 1548022 | 7/1979 |
| WO | WO 91/04757 | 4/1991 |
| WO | WO 93/13074 | 7/1993 |
| WO | WO 00/67694 | 11/2000 |
| WO | WO 02/39991 | 5/2002 |
| WO | WO 03/030881 | 4/2003 |

OTHER PUBLICATIONS

Funck-Bretano et al. Circulation 1991;83;536-545.*
Huupponen et al., "Buccal Delivery of an $\alpha_2$-adrenergic Receptor Antagonist, Atipamezole, in Humans," 58 *Clin Pharmacol Ther* 506 (1995).
Farmos, "Atipamezole Antisedan®," 21 *Drugs of the Future* 534 (1996).
Sorbera et al., "Fipamezole Hydrochloride," 28 *Drugs of the Future* 14 (2003).
Penttila et al., "Effects of Atipamezole—A Selective α2-Adrenoceptor Antagonist—on Cardiac Parasympathetic Regulation in Human Subjects," 24 *Autonomic & Autocoid Pharm.* 69-75.
Takuri et al., "Preservation of Dispersed Systems," 2 *Pharmaceutical Dosage Forms* 73-114 (Lieberman, Rieger and Banker eds. 1989).
Crouch et al., "Clinical Relevance and Management of Drug-Related QT Interval Prolongation," 23 Pharmacotherapy 881-908 (2003).
Myerburg, ch 232 "Electrocariography", Harrison's Internal Medicine 999 (Isselbacher, Adams, Braunwald, Petersdorf & Wilson eds, McGraw-Hill, pp. 999-1011; 9th ed. 1981).
"Guidance for Industry, S7B Nonclinical Evaluation of the Potential for Delayed Ventricular Repolarization" (USFDA Oct. 2005).
FDA Center for Drug Evaluation and Research Data Standards Manual (Jan. 11, 2006).

* cited by examiner

*Primary Examiner* — Shirley V Gembeh
(74) *Attorney, Agent, or Firm* — James C. Lydon

(57) ABSTRACT

An oromucosal formulation containing as an active ingredient a substituted imidazole derivative of formula (I)

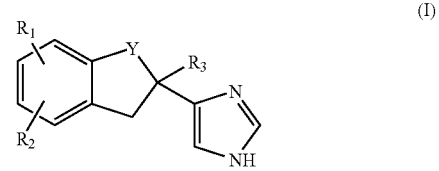

(I)

where Y is —$CH_2$— or —CO—, $R_1$ is halogen or hydroxy, $R_2$ is H or halogen and $R_3$ is H or lower alkyl, or an acid addition salt of this imidazole derivative, and a process for its preparation.

10 Claims, 1 Drawing Sheet

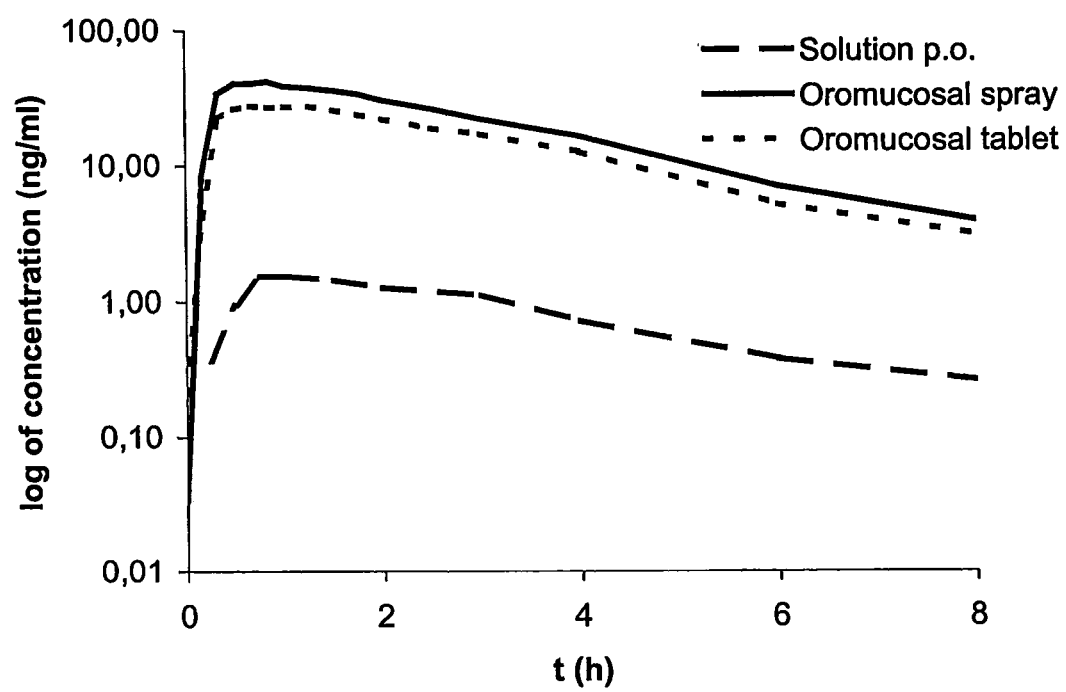

OROMUCOSAL FORMULATION AND PROCESS FOR PREPARING THE SAME

FIELD OF THE INVENTION

The present invention relates to an oromucosal formulation comprising as an active ingredient a substituted imidazole derivative of formula (I)

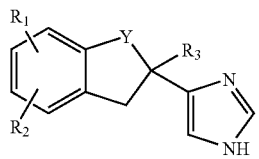

(I)

wherein Y is —$CH_2$— or —CO—, $R_1$ is halogen or hydroxy, $R_2$ is H or halogen and $R_3$ is H or lower alkyl, or an acid addition salt thereof.

The invention also relates to a process for preparing the oromucosal formulation in question.

BACKGROUND OF THE INVENTION

The compounds of the above-mentioned formula (I) are highly selective and long-acting antagonists of $\alpha_2$-adrenoceptors. The compounds are especially valuable in the treatment of cognitive disorders. Compounds of formula (I) and their preparation have been described in patent publication EP 0 618 906 B1. Specific examples of such compounds are 4-(2-ethyl-5-fluoroindan-2-yl)-1H-imidazole, i.e. fipamezole, and 4-(5-fluoroindan-2-yl)-1H-imidazole.

Although the compounds of formula (I) and their salts have good properties as such, they have disadvantages, when formulated for conventional oral administration, i.e. the normal route for administering said compounds. A problem is that the compounds rather quickly decompose in the gastrointestinal area or other body systems prior to accessing systemic blood flow and the therapeutic target organs. This in turn significantly lowers the effect of the compounds in question.

Toxicology studies carried out with dogs (see Example 8) have further suggested that cardiac safety considerations are of importance whereas QT prolongation was observed with high oral doses of fipamezole when the systemic concentration of fipamezole reached about 2000 ng/ml.

OBJECT AND SUMMARY OF THE INVENTION

One object of the present invention is to provide a formulation for administering compounds of formula (I) safely and efficiently.

Another object of the present invention is to provide a process for preparing the formulation.

Thus, according to one aspect of this invention concerns an oromucosal formulation comprising as an active ingredient a substituted imidazole derivative of formula (I)

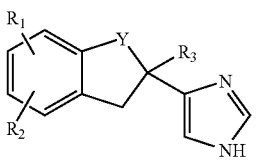

(I)

where Y is —$CH_2$— or —CO—, $R_1$ is halogen or hydroxy, $R_2$ is H or halogen and $R_3$ is H or lower alkyl, or an acid addition salt thereof, together with additives conventionally used in oromucosal formulations.

According to another aspect, the invention concerns a process for preparing the oromucosal formulation.

DETAILED DESCRIPTION OF THE INVENTION

It has now surprisingly been found that the problems of quick decomposition in the gastrointestinal area and compromised cardiac safety of the compounds of formula (I) can be alleviated by formulating the compounds of formula (I) into oromucosal formulations. Such formulations are effective and easy to handle, and therefore they have an advantage in terms of practical administration to the patient.

Suitable additives to be used in the formulation according to the present invention are adjuvants, excipients etc. including solvents, preserving agents, flavouring agents, fillers, gelling agents and mucoadhesive polymers. Preferred solvents are alcohols, especially ethanol, water and mixtures thereof. Preferred preserving agents are lower alkyl parahydroxybenzoates, especially methyl and propyl parahydroxybenzoate, and mixtures thereof. Preferred flavouring agents are aspartame, artificial flavours, such as black currant 502.009, and mixtures thereof.

In this context, the oromucosal formulation means any type of formulation administered via oral mucosa. Such formulations include e.g. sprays, gels, mucoadhesive buccal tablets and pastes, sublingual tablets and like. The formulation is preferably in the form of a spray.

In this context, the term halogen refers to F, Cl, Br and I, preferably to F and Cl and most preferably to F.

In this context, the term lower alkyl refers to a monoradical branched or unbranched saturated hydrocarbon chain having from 1 to 6 carbon atoms, preferably 1 to 4 carbon atoms and most preferably 1 or 2 carbon atoms.

In this context, the term an acid addition salt refers to an addition salt of any pharmaceutically acceptable acid, preferably hydrochloric acid.

In this context, the term an additive conventionally used in oromucosal formulations refers to any additive known by the person skilled in the art to be applicable for oromucosal formulations.

An especially preferred active ingredient is fipamezole (JP-1730, 4-(2-ethyl-5-fluoroindan-2-yl)-1H-imidazole hydrochloride). A formulation containing said preferred active ingredient is prepared according to the invention by mixing and dissolving ethanol (96%), purified water, methylparahydroxybenzoate, propylparahydroxybenzoate and aspartame at room temperature, at +15 to +25° C. Followed by adding and dissolving 4-(2-ethyl-5-fluoroindan-2-yl)-1H-imidazole and artificial flavour, such as black currant 502.009A, at room temperature, at +15 to +25° C. The volume of the mixture is adjusted with purified water, followed by filtering and the desired spray formulation is recovered.

The following examples illustrate the invention, but are not intended to restrict the scope of the invention.

Example 1

Spray Formulation Containing 4-(2-ethyl-5-fluoroindan-2-yl)-1H-imidazole hydrochloride (fipamezole)

Fipamezole Oromucosal Spray

| Ingredient | Quantity per 1 ml | Function |
|---|---|---|
| Fipamezole | 15.0 mg | Active |
| Methyl parahydroxybenzoate | 1.8 mg | Preservative |
| Propyl parahydroxybenzoate | 0.2 mg | Preservative |
| Aspartame | 0.5 mg | Flavouring agent |
| Artificial flavour* | 0.4 mg | Flavouring agent |
| Ethanol (96%) | 0.416 ml | Solvent |
| Purified water | ad 1.0 ml | Solvent |

*Artificial flavour, such as black currant 502.009A, for example, but not restricted to.

Example 2

Spray Formulation Containing 4-(2-ethyl-5-fluoroindan-2-yl)-1H-imidazole hydrochloride (fipamezole)

Fipamezole Oromucosal Spray

| Ingredient | Quantity per 1 ml | Function |
|---|---|---|
| Fipamezole | 161.0 mg | Active |
| Methyl parahydroxybenzoate | 1.8 mg | Preservative |
| Propyl parahydroxybenzoate | 0.2 mg | Preservative |
| Aspartame | 0.5 mg | Flavouring agent |
| Artificial flavour* | 0.4 mg | Flavouring agent |
| Ethanol (96%) | 0.416 ml | Solvent |
| Purified water | ad 1.0 ml | Solvent |

*Artificial flavour, such as black currant 502.009A, for example, but not restricted to.

Example 3

Preparation of a Spray Formulation Containing 4-(2-ethyl-5-fluoroindan-2-yl)-1H-imidazole hydrochloride (fipamezole)

416.0 ml of ethanol (96%) was mixed with 450.0 ml of purified water to form a homogenous mixture. 1.80 g of methylparahydroxybenzoate, 0.20 g of propylparahydroxybenzoate and 0.5 g of aspartame were added to the mixture and dissolved at room temperature, at +15 to +25° C. 15.0 g of fipamezole, 0.4 g of black currant flavour were added to the mixture and dissolved at room temperature, at +15 to +25° C. The volume of the mixture was adjusted to 1000.0 ml with purified water. The solution was filtered and the desired spray formulation was recovered.

Example 4

Preparation of an Oromucosal Gel Formulation Containing 4-(2-ethyl-5-fluoroindan-2-yl)-1H-imidazole hydrochloride (fipamezole) 30 mg Composition

| | Ingredient | Amount/single dose |
|---|---|---|
| 1 | Fipamezole | 30 mg |
| 2 | Ethanol (96%) | 250 mg |
| 3 | Poloxamer 407 | 200 mg |
| 4 | Liquid flavour (artificial) | 0.5 mg |
| 5 | Aspartame (sweetener) | 0.5 mg |
| 6 | Purified water | 519 mg |
| | Total of | 1000 mg |

Method of Preparation

Fipamezole (1) and ethanol (96%) (2) are mixed and dissolved to form a solution A. Purified water (6), poloxamer 407 (3), liquid flavour (4), and aspartame (5) are mixed and dissolved to form a solution B. Solution A and solution B are cooled down to approx. +5° C., and mixed together to form a homogenous solution. Oromucosal gel formulation is recovered.

Example 5

Preparation of a Mucoadhesive Buccal Tablet Formulation Containing 4-(2-ethyl-5-fluoroindan-2-yl)-1H-imidazole hydrochloride fipamezole) 30 mg Composition

| | Ingredient | Amount/single dose |
|---|---|---|
| 1 | Fipamezole | 30 mg |
| 2 | Carbomer 934P | 12.35 mg |
| 3 | Hydroxypropylmethylcellulose | 49.4 mg |
| 4 | Flavour (artificial) | 4 mg |
| 5 | Aspartame (sweetener) | 4 mg |
| 6 | Magnesium stearate | 0.25 mg |
| | Total of | 100 mg |

Method of Preparation

Fipamezole (1), carbomer 934P (2), hydroxypropylmethyl-cellulose (3), flavour (4), aspartame (5), and magnesium stearate (6) are mixed to form a homogenous mixture. The mixture is compressed to tablets of a suitable size. Mucoadhesive buccal tablets are recovered.

Example 6

Preparation of a Sublingual Tablet Formulation Containing 4-(2-ethyl-5-fluoroindan-2-yl)-1H-imidazole hydrochloride (fipamezole) 30 mg Composition

| | Ingredient | Amount/single dose |
|---|---|---|
| 1 | Fipamezole | 30 mg |
| 2 | Lactose monohydrate | 30 mg |
| 3 | Povidone | 2.4 mg |
| 4 | Microcrystalline cellulose | 10.8 mg |

-continued

| | Ingredient | Amount/single dose |
|---|---|---|
| 5 | Flavour | 3.2 mg |
| 6 | Aspartame (sweetener) | 3.2 mg |
| 7 | Magnesium stearate | 0.4 mg |
| | Total of | 80 mg |

Method of Preparation

Fipamezole (1), lactose monohydrate (2), flavour (5), and aspartame (6) are mixed to form a homogenous mixture. The mixture is granulated with 10% aqueous solution of povidone (3). Granules are formed in either high-shear or low-shear mixer. Granulated mixture is let to dry. Dry, granulated mixture is passed through a screen to obtain freely flowing granulate. Microcrystalline cellulose (4) and magnesium stearate (7) are mixed with the granulate. The final blend is compressed to tablets of a suitable size. Sublingual tablets are recovered.

Example 7

Oromucosal Delivery of Fipamezole

Plasma levels of fipamezole were studied in healthy male volunteers after oral administration of the drug as a solution. Blood samples for pharmcokinetic evaluation were collected for 24 hours after the drug administration. The concentration of fipamezole in plasma was measured with HPLC-MS/MS, and the pharmacokinetic parameters were calculated. The pharmacokinetics of fipamezole was evaluated with TopFit 2.0 pharmacokinetic program. The $C_{max}$ and $t_{max}$ values were read from the concentration vs. time curves, and the apparent elimination phase half-lives from the terminal part of the semilogarithmic concentration vs. time curve (see FIG. 1). AUC values were calculated both to infinity and up to the last collection time with quantifiable fipamezole concentration. The results are given in Table 1.

TABLE 1

Mean (SD) pharmacokinetic parameters of fipamezole at the dose level of 30 mg. $t_{max}$ values are given as median and range.

| 30-mg dosing | $C_{max}$ (ng/ml) | $t_{max}$ (h)a | $t_{1/2el}$ (h) | $AUC_{0-inf}$ (ng * h/ml) |
|---|---|---|---|---|
| Oral | 1.59 (0.38) | 1.0 (0.75-2.0) | 3.10 (2.23) | 7.65 (2.99) |
| Oromucosal, tablet | 31.74 (13.50) | 0.85 (0.43) | 3.10 (1.00) | 115.6 (41.10) |
| Oromucosal, spray | 49.2 (11.0) | 0.7 (0.5-1.0) | 2.10 (0.20) | 157.1 (24.7) |

$C_{max}$, maximal drug concentration in serum;
$t_{max}$, time of maximal drug concentration in serum;
$t_{1/2el}$, apparent elimination phase half-life;
$AUC_{0-inf}$, area under the drug concentration in serum vs. time curve from time 0 to infinity.

Mean plasma concentration time plot following single dose administration of 30 mg fipamezole via an oral, oromucosal spray and an oromucosal tablet on a semilogarithmic scale is shown in FIG. 1.

Example 8

Cardiac Safety

Cardiac safety was studied in dogs in a 30-day dog toxicology study using oral dosing and dog toxicology studies using buccal dosing.

In the 30-day dog toxicology study fipamezole was administered orally at doses of 1, 5, 10 and 15 mg/kg/day for 30 days, resulting in maximum systemic fipamezole concentrations of about 200, 1000, 2000 and 3300 ng/ml, respectively. These in vivo results in the dog suggested that QT prolongation was observed when the systemic concentration of fipamezole reached about 2000 ng/ml.

In another toxicology study four male dogs were given fipamezole in buccal spray doses of 1, 5 and 10 mg/kg in a sequential dosing regimen with 5 to 15 days between doses. Blood pressure (systolic, diastolic and mean), heart rate and ECGs were monitored before and up to 12 hours after dosing. At 30 minutes after dosing with 5 and 10 mg/kg significant transient increases in absolute values for blood pressure and heart rate were observed. No ECG changes (P wave amplitude, P wave duration, P-Q interval, QRS interval or Q-T [Q-Tcv, QTc] interval) were apparent after fipamezole dosing at each dose level.

Yet another toxicology study using buccal delivery to dogs at dose levels of 1, 5 and 10 mg/kg/day for up to 4 weeks showed no apparent changes in ECG. Maximum systemic concentrations of fipamezole after dosing on the first day of this study were about 800, 2000 and 3300 ng/ml.

The invention claimed is:

1. A method of administering a formulation comprising as an active ingredient a substituted imidazole of formula (I)

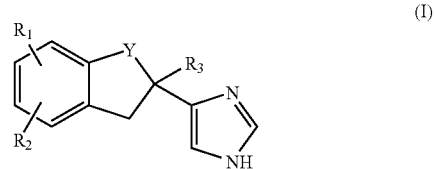

(I)

where Y is —$CH_2$— or —CO—, $R_1$ is halogen or hydroxy, $R_2$ is H or halogen and $R_3$ is H or lower alkyl, or an acid addition salt thereof, comprising
administering said formulation to a patient by oromucosal administration, wherein oromucosal administration is absorption via oral mucosa, and wherein said active ingredient is 4-(2-ethyl-5-fluoro-indan-2-yl)-1H-imidazole or its acid salt.

2. The method of claim 1, wherein said active ingredient is a hydrochloride salt of 4-(2-ethyl-5-fluoro-indan-2-yl)-1H-imidazole.

3. The method of claim 1, wherein said formulation includes at least one additive selected from the group consisting of solvents, preserving agents, flavoring agents and mixtures thereof.

4. The method of claim 3, wherein the solvent is selected from the group consisting of ethanol, water and a mixture thereof.

5. The method of claim 3, wherein the preserving agent is selected from the group consisting of methyl parahydroxybenzoate, propyl parahydroxybenzoate and a mixture thereof.

6. The method of claim 3, wherein the flavoring agent is selected from the group consisting of aspartame, black currant and a mixture thereof.

7. The method of claim 3, wherein said additive is a flavoring agent.

8. The method of claim 1, wherein said formulation comprises the following components: (a) 4-(2-ethyl-5-fluoro-indan-2-yl)-1H-imidazole or its acid salt, (b) ethanol and water, (c) methyl parahydroxybenzoate and propyl parahydroxybenzoate, and (d) aspartame and black currant.

9. The method of claim 1, wherein the formulation is administered in the form of a spray, gel, a mucoadhesive buccal tablet or paste, or a sublingual tablet.

10. The method of claim 9, wherein the formulation is administered in the form of a spray.

* * * * *